United States Patent [19]
Stürmer et al.

[11] Patent Number: 6,063,615
[45] Date of Patent: May 16, 2000

[54] ENZYMATIC ACYLATION OF AMINO ACID ESTERS USING A CARBOXYLIC ACID ESTER SUBSTITUTED WITH OXYGEN ON THE ALPHA CARBON

[75] Inventors: Rainer Stürmer, Rödersheim-Gronau; Klaus Ditrich, Gönnheim; Wolfgang Siegel, Limburgerhof, all of Germany

[73] Assignee: BASF Aktiengesellschaft, Ludwigshafen, Germany

[21] Appl. No.: 09/104,173

[22] Filed: Jun. 25, 1998

[51] Int. Cl.[7] .............................. C12P 13/04; C12P 13/24; C12P 13/22; C12P 13/14; C07C 1/04

[52] U.S. Cl. .................. 435/280; 435/106; 435/107; 435/108; 435/109; 435/110; 435/113; 435/114; 435/115; 435/116

[58] Field of Search ........................ 435/280, 106, 435/107, 108, 109, 110, 113, 114, 115, 116

[56] References Cited

U.S. PATENT DOCUMENTS

| | | | |
|---|---|---|---|
| 5,057,607 | 10/1991 | Zmijewski et al. | 540/364 |
| 5,728,876 | 3/1998 | Balkenhohl et al. | 435/280 |

FOREIGN PATENT DOCUMENTS

| | | |
|---|---|---|
| 95/08636 | 3/1995 | WIPO . |
| 96/23894 | 8/1996 | WIPO . |

OTHER PUBLICATIONS

Pugniere et al., "Racemization of Amino Acid Esters Catalyzed by Pyridoxal 5' phosphate as a Step in the Production of L–Amino Acids", Biotechnol. Lett. 5(7): 447–52 (1983).

Fache et al., "A Catalytic Stereo–and Chemo–Selective Method for the Reduction of Substituted Aromatics", *Tetrahedron Lett.*, 36(6), 1995, 885–888.

Sim et al., "Combinatorial Synthesis of 2–Thioxo–4–dihydropyrimidinones", *J. Org. Chem.*, 62(26), 1997, 9358–9360.

Bernath et al., "Synthesis and Steric Structures of Perhydro–4,1–Benzoxapin–3–ones", *Tetrahedron*, 43(19), 1987, 4359–4366.

Kanerva et al., "Approach to Highly Enantiopure Beta–Amino Acid Esters by Using Lipase Catalysis in Organic Media", *Tetrahedron Asymmetry*, 7(6), 1996, 1705–1716.

Orsat et al., "Homocarbonates as Substrates for the Enantioselective Enzymatic Protection of Amines", *J. Am. Chem. Soc.*, 118, 1996, 712–13.

Asensio et al., "Enzyme–mediates enantioselective acylation of secondary amines in organic solvents", *Tetrahedron Letters*, 32(33), 1991, 4197–4198.

J. Prakt. Chem. 339 (1997) 381–384, Balkenhohl et al.

Tetrahedron: Asymmetry, vol. 8, No. 1, 37–40, 1997 Sanchez et al.

*Primary Examiner*—Sandra E. Saucier
*Attorney, Agent, or Firm*—Keil & Weinkauf

[57] ABSTRACT

Disclosed is a process for preparing acylated amino esters and a process for preparing optically active amino esters from racemic amino esters with a carboxylic ester as acylating agent, whose acid component has a halogen, nitrogen, oxygen or sulfur atom neighboring the carbonyl carbon atom, in the presence of a hydrolase selected from the group of amidase, protease, esterase and lipase, and subsequent separation of the enantioselectively acylated amino ester from the non-acylated other enantiomer of the amino ester.

5 Claims, No Drawings

ENZYMATIC ACYLATION OF AMINO ACID ESTERS USING A CARBOXYLIC ACID ESTER SUBSTITUTED WITH OXYGEN ON THE ALPHA CARBON

BACKGROUND OF THE INVENTION

The present invention relates to a process for preparing acylated amino esters and to a novel process for preparing optically active amino esters from racemic amino esters with a carboxylic ester as acylating agent, whose acid component has a halogen, nitrogen, oxygen or sulfur atom neighboring the carbonyl carbon atom, in the presence of a hydrolase selected from the group of amidase, protease, esterase and lipase, and subsequent separation of the enantioselectively acylated amino ester from the non-acylated other enantiomer of the amino ester.

Resolution of racemic primary and secondary amines by reaction with a carboxylic ester in the presence of a hydrolase is described in WO 95/08636 and WO 96/23894, and in a review article by Balkenhohl et al. in J. prakt. Chem. 339 (1997) 381–384. The preferred amines mentioned therein are primary arylalkylamines and heteroatom-substituted amines. However, no reference to the usability of amino esters is to be found in any of the three publications.

Gotor et al. (Tetrahedron: Asymmetry, 1997, 37–40) describe the enantioselective acylation of ethyl 3-aminobutyrate with ethyl acetate catalyzed by *Candida antarctica* Lipase (SP 435). However, the amounts of enzyme required for the catalysis are enormous (50% of the weight of the substrate), so that a process based on this is not economic. In addition, the enantioselectivity of the process is too low. It achieves selectivity only in the region of E=70–90.

SUMMARY OF THE INVENTION

It is an object of the present invention to provide a process for the enzyme-catalyzed resolution of racemic amino esters which ensures high enantioselectivity, can be employed in a wide range of reaction conditions, and moreover makes do with minimal amounts of catalyst.

We have found that this object is achieved by a process for resolving racemic amino esters by reaction with a carboxylic ester as acylating agent with specific catalysis by a hydrolase selected from the group of amidase, protease, esterase and lipase, and subsequent separation of the enantioselectively acylated amino ester from the non-acylated other enantiomer of the amino ester, wherein the acid component of the carboxylic ester used as acylating agent has an electron-rich heteroatom selected from the group formed by halogen, nitrogen, oxygen and sulfur atoms and neighboring the carbonyl carbon atom.

We have furthermore found a process for preparing acylated amino esters by reacting the amino esters with a carboxylic ester as acylating agent with specific catalysis by a hydrolase selected from the group of amidase, protease, esterase and lipase, wherein the acid component of the ester has a halogen, nitrogen, oxygen or sulfur atom neighboring the carbonyl carbon atom.

DETAILED DESCRIPTION OF THE INVENTION

The carboxylic esters suitable as acylating agents for the novel process are those having, in the acid component of the ester, an electron-rich heteroatom neighboring the carbonyl carbon.

The heteroatom must have at least one free pair of electrons. It may be a halogen, in particular chlorine or fluorine, nitrogen, oxygen or sulfur atom.

It is to be located in the neighborhood of the carbonyl carbon. By this is meant linkage of the heteroatom to a carbon atom in the position alpha, beta or gamma to the carbonyl carbon. Preferred acid components of the ester are those in which the heteroatom is linked to the alpha carbon atom. Oxygen is preferred as heteroatom.

The heteroatom may, where appropriate, be attached to other groups, eg. alkyl or aryl groups, preferably alkyl groups. If the heteroatom is oxygen, for example, an ether group is present.

It is possible to use as alcohol component of the ester for the novel process branched and unbranched $C_1$–$C_{10}$-alcohols, preferably $C_1$–$C_6$-alcohols, particularly preferably $C_2$–$C_5$-alcohols, which may also be substituted.

Particularly suitable carboxylic esters are those of the formula III

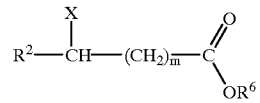

where
$R^2$ is H, $C_{1-C10}$-alkyl,
X is halogen, $OR^3$, $SR^3$, $NR^3R^4$,
$R^3$ is H, $C_1$–$C_{10}$-alkyl, aryl, unsubstituted or substituted by $NH_2$, OH, $C_1$–$C_4$-alkyl, $C_1$–$C_4$-alkoxy or halogen,
$R^4$ is H, $C_1$–$C_{10}$-alkyl, aryl, unsubstituted or substituted by $NH_2$, OH, $C_1$–$C_4$-alkyl, $C_1$–$C_4$-alkoxy or halogen,
$R^6$ is $C_1$–$C_{10}$-alkyl,
m is 0, 1 or 2.

Particularly preferred among these are the $C_1$–$C_4$-alkyl esters of $C_1$–$C_4$-alkoxyacetic acids, such as ethyl methoxyacetate or isopropyl methoxyacetate.

A large number of enzymes car be employed as hydrolases in the novel process. Amidases, proteases, esterases and lipases, especially lipases, are preferably used. Particularly suitable lipases are microbial lipases which can be isolated, for example, from yeasts or bacteria. Very particularly suitable lipases are those from Pseudomonas, eg. Amano P or the lipase from Pseudomonas spec. DSM 8246. Further very particularly suitable hydrolases are the enzymes commercially obtainable from Novo Nordisk (Enzyme Toolbox), especially the lipases SP 523, SP 524, SP 525, SP 526 and Novozym® 435. These enzymes are microbial lipases which can be produced from yeasts such as *Candida antarctica*.

The enzyme can be employed in native or in immobilized form. The immobilized enzyme Novozym® 435 is particularly suitable.

The novel process can be carried out using solvents or, in the case of liquid amino esters, also without solvent.

Organic solvents are generally suitable as solvents. The reaction takes place particularly well in ethers, for example in MTBE (=methyl; tert-butyl ether) or THF (=tetrahydrofuran), or in hydrocarbons such as hexane, cyclohexane, toluene or halogenated hydrocarbons such as methylene chloride. It is also possible to add propylene carbonate, acetonitrile or dioxane if the precursors are of low solubility.

The enzyme-catalyzed reaction of the carboxylic ester with the racemic amino ester is normally carried out at from 20 to 50° C., in particular from 25 to 35° C. Depending on the amino ester, the reaction takes from 1 to 48, preferably 4 to 24, hours. Secondary amino esters as a rule require longer reaction times than do primary amino esters. The lower reactivity of secondary amino esters may also be compensated by increasing the amount of catalyst by comparison with primary amino esters.

The amino ester is employed in a concentration of from 5 to 50%, preferably from 10 to 30%, of the total weight of the reaction mixture.

From 1 to 3 mol, preferably 1 to 2 mol, particularly preferably 1 to 1.5 mol, of carboxylic ester are added per mole of amino ester to be reacted.

The amount of enzyme to be added depends on the nature of the hydrolase and the activity of the enzyme preparation. The optimal amount of enzyme for the reaction can easily be determined by simple preliminary tests.

The course of the reaction can easily be followed by conventional methods, for example by gas chromatography. In the case of the racemate resolution, it is sensible to stop the reaction when 50% of the recemic amino ester has reacted. As a rule, this takes place by removing the catalyst from the reaction, for example by filtering off the enzyme.

The enantioselective reaction of the racemic amino ester with the carboxylic ester used as acylating agent results in the acylated product (amide) corresponding to one enantiomer, while the other enantiomer remains unchanged. The resulting mixture of amino ester and N-acylated derivative can easily be separated by conventional methods. Extraction or distillation processes, for example, are very suitable for separating the mixture.

The novel process is suitable for acylating and for resolving racemates of α-, β- and γ-amino esters. The resolution of racemic β-amino esters takes place particularly well, especially with cyclic β-amino esters of the following formula IV

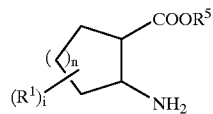

IV where $R^5$ is $C_1$–$C_{10}$-alkyl, preferably $C_1$–$C_6$-alkyl, particularly preferably $C_2$–$C_5$-alkyl, and is aryl, preferably phenyl or benzyl, which is unsubstituted or substituted by $NH_2$, OH, $C_1$–$C_4$-alkyl, $C_1$–$C_4$-alkoxy or halogen, and n can assume values from 1 to 3.

The carbocyclic system may be substituted by $R^1$, where $R^1$ is $C_1$–$C_{10}$-alkyl, preferably $C_1$–$C_6$-alkyl, particularly preferably $C_2$-$C_5$-alkyl, $C_1$–$C_4$-alkoxy, OH, $NH_2$, halogen, preferably Cl, and is furthermore aryl, unsubstituted or substituted by $NH_2$, OH, $C_1$–$C_4$-alkyl, $C_1$–$C_4$-alkoxy or halogen, preferably phenyl or benzyl. The number of substituents $R^1$ is determined by the index i and may be from 0 to 4.

The invention is also suitable for preparing optically active amino esters from racemic amino esters by
  a) enantioselectively acylating a racemic amino ester with a carboxylic ester as acylating agent whose acid component has a fluorine, nitrogen, oxygen and sulfur atom neighboring the carbonyl carbon atom, in the presence of a hydrolase,
  b) separating the mixture of optically active amino ester and optically active N-acylamino ester and thus obtaining one enantiomer of the amino ester,
  c) where appropriate obtaining the other enantiomer of the amino ester from the N-acylamino ester by amide cleavage.

The novel process can be made even more economic if, after removal of the required enantiomer, the remaining unwanted enantiomer is racemized and employed anew in the process. Thus, for example, an unwanted acylated amino ester can be racemized in the presence of non-nucleophilic bases such as potassium tert-butoxide, and converted by a strong acid (mineral acid) into the free racemic amino ester. This recycling makes it possible to obtain overall more than 50% of the required enantiomer from the racemic amine.

Not only is the novel process suitable for preparing optically active amino esters, but it can also form part of complicated chemical multistage syntheses, for example In the preparation of medicinal agents or crop protection agents.

The present invention thus also relates to optically active amino esters of the formula I

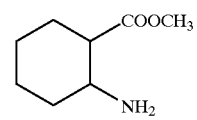

I where the $NH_2$ group and the methoxycarbonyl radical are in either the cis or the trans position with respect to one another. The two substituents are preferably in the trans position with respect to one another.

The present invention likewise relates to optically active N-acylamino esters of the formula II

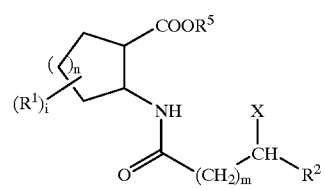

II where the radicals have the following meanings:
  $R^1$ $C_1$–$C_{10}$-alkyl, $C_1$–$C_4$-alkoxy, OH, $NH_2$, halogen, aryl, unsubstituted or substituted by $NH_2$, OH, $C_1$–$C_4$-alkyl, $C_1$–$C_4$-alkoxy or halogen
  $R^2$ H, $C_1$–$C_{10}$-alkyl
  X halogen, $OR^3$, $SR^3$, $NR^3R^4$,
  $R^3$ H, $C_1$–$C_{10}$-alkyl, aryl, unsubstituted or substituted by $NH_2$, OH, $C_1$–$C_4$-alkyl, $C_1$–$C_4$-alkoxy or halogen
  $R^4$ H, $C_1$–$C_{10}$-alkyl, aryl, unsubstituted or substituted by $NH_2$, OH, $C_1$–$C_4$-alkyl, $C_1$–$C_4$-alkoxy or halogen
  $R^5$ $C_1$–$C_{10}$-alkyl, aryl, unsubstituted or substituted by $NH_2$, OH, $C_1$–$C_4$-alkyl, $C_1$–$C_4$-alkoxy or halogen
  i 0 to 4
  m 0, 1 or 2
  n 1 to 3
    and where the acylamino group and the $COOR^5$ radical can be either cis or trans with respect to one another.

Preferred radicals for X are chlorine or $OR^3$, where $R^3$ is $C_1$–$C_4$-alkyl. $R^5$ is preferably $C_2$–$C_5$-alkyl and phenyl or benzyl, each of which is unsubstituted or substituted by $NH_2$, OH, $C_1$–$C_4$-alkoxy or halogen.

The following examples serve to illustrate the invention.

EXAMPLE 1

Resolution of Racemic Methyl Trans-2-aminocyclohexanecarboxylate 50 g (0.32 mol) of methyl trans-2-aminocyclohexanecarboxylate were dissolved in 200 ml of MTBE and, after addition of 0.16 mol of isopropyl methoxyacetate and 0.5 g of Novozym 435 (Novo Nordisk), shaken at room temperature for 8 h. The enzyme was filtered off and then the solvent was removed and the residue was distilled under reduced pressure. 23.5 g of methyl (1S,2S)-2-aminocyclohexanecarboxylate and 35.2 g of methyl (1R,2R)-2-(2-methoxyacetylamino) cyclohexanecarboxylate were obtained, each with an ee of 99.8%. The ee of the amine was determined after N-acylation with acetic anhydride by gas chromatography on a B-PH GC column (supplied by Astec, N.J., USA), while the N-2-methoxyacetamide was put on this column without derivatization.

EXAMPLE 2
Resolution of Racemic Phenylalanine Methyl Ester 8.4 g (0.5 mol) of recemic phenylalanine methyl ester were dissolved in 500 ml of MTBE and, after addition of 0.51 mol of ethyl methoxyacetate and 0.8 g of Novozym 435 (Novo Nordisk), shaken at room temperature for 8 h. The enzyme was filtered off and then the non-acylated (S)-phenylalanine methyl ester was removed by extracting with 150 ml of 2M HCl and was subsequently isolated from the acidic aqueous phase by treatment with 160 ml of 2M NaOH followed by extraction with 1 l of ethyl acetate. The acylated enantiomer was isolated directly from the reaction solution by evaporating off the solvent. 37.12 g (0.21 mol) of (S)-phenylalanine methyl ester with an ee of 99% and 57.78 g (0.23 mol) of the corresponding (N)-methoxyacetamide of (R)-phenylalanine methyl ester with an ee of 97.5% were obtained.

EXAMPLE 3
Resolution of Racemic Ethyl 3-aminobutyrate 13.1 g (0.1 mol) of racemic ethyl 3-aminobutyrate were dissolved in 60 ml of MTBE and, after addition of 0.05 mol of isopropyl methoxyacetate and 130 mg of Novozym 435 (Novo Nordisk), shaken at room temperature for 12 h. The enzyme was filtered off and then the solvent was removed and the residue was distilled under reduced pressure 5.37 g (0.041 mol) of ethyl (3S)-3-aminobutyrate with an ee of 98.5% and 9.10 g (0.045 mol) of the corresponding (N)-methoxyacetamide of ethyl (3R)-3-aminobutyrate with an ee of >99% were obtained.

We claim:

1. A process for preparing acylated amino esters by reacting the amino esters with an acylating agent in the presence of a hydrolase selected from the group of protease, esterase and lipase, wherein the acylating agent is a carboxylic ester whose acid component has an oxygen atom in the position alpha to the carbonyl carbon atom.

2. A process for preparing optically active amino esters from racemic amino esters, which comprises a) enantioselectively acylating a racemic amino ester with a carboxylic ester as acylating agent whose acid component has an oxygen atom in the position alpha to the carbonyl carbon atom, in the presence of a hydrolase selected from the group of protease, esterase and lipase, and b) separating the mixture of optically active amino ester and optically active N-acylamino ester and thus obtaining one enantiomer of the amino ester.

3. The process of claim 2, wherein, following the step b), the unwanted enantiomer is racemized in another step, and this racemic mixture is returned to step a).

4. The process of claim 2 further comprising a step c) following step b) of cleaving the amide bond of the N-acylamino ester yielding unwanted enantiomer.

5. The process of claim 4, wherein, following the step b) or c), the unwanted enantiomer is racemized in another step, and this racemic mixture is returned to step a).

* * * * *

UNITED STATES PATENT AND TRADEMARK OFFICE
CERTIFICATE OF CORRECTION

PATENT NO.: 6,063,615

DATED: May 16, 2000

INVENTOR(S): STUERMER et al.

It is certified that error appears in the above-identified patent and that said Letters Patent is hereby corrected as shown below:

cover page:

--[30] Foreign Application Priority Data

June 30, 1997 [DE] Germany ........................ 197 27 517.6--.

Signed and Sealed this

Third Day of April, 2001

Attest:

NICHOLAS P. GODICI

Attesting Officer

Acting Director of the United States Patent and Trademark Office